US006129174A

United States Patent [19]

Brown et al.

[11] Patent Number: 6,129,174

[45] Date of Patent: Oct. 10, 2000

[54] MINIMAL CONTACT REPLACEABLE ACOUSTIC COUPLER

[75] Inventors: Joseph Brown, Valley Center; Scott Rouw, Union City; Gregory A. Anderson, Fremont, all of Calif.

[73] Assignee: Decibel Instruments, Inc., Fremont, Calif.

[21] Appl. No.: 09/224,817

[22] Filed: Dec. 30, 1998

[51] Int. Cl.[7] .................... A61B 7/02

[52] U.S. Cl. .................... 181/135; 381/325

[58] Field of Search .................... 181/135, 129, 181/131; 381/322, 325, 324, 328

[56] References Cited

U.S. PATENT DOCUMENTS

| | | | |
|---|---|---|---|
| 2,803,308 | 8/1957 | Mattia | 181/131 |
| 4,607,720 | 8/1986 | Hardt . | |
| 4,880,076 | 11/1989 | Ahlberg et al. . | |
| 5,002,151 | 3/1991 | Oliveira et al. . | |
| 5,031,219 | 7/1991 | Ward et al. . | |
| 5,201,007 | 4/1993 | Ward et al. . | |
| 5,654,530 | 8/1997 | Sauer et al. . | |
| 5,742,692 | 4/1998 | Garcia et al. . | |
| 5,748,743 | 5/1998 | Weeks . | |
| 5,824,968 | 10/1998 | Packard et al. | 181/135 |

*Primary Examiner*—Khanh Dang
*Attorney, Agent, or Firm*—Michael A. Glenn; Christopher Peil

[57] ABSTRACT

An acoustic coupler adapted for use with an intracanal receiver module can be deeply inserted into the ear canal of the user while making minimal contact with the walls of the ear canal. The minimal contact feature of the invention allows the acoustic coupler to seal the ear canal acoustically and anchor a hearing device at an optimal depth within the ear canal, while maximizing the user's comfort. The acoustic coupler is manufactured from a soft, pliable elastomer that allows it to conform readily to the shape of the ear canal. The acoustic coupler incorporates structural supports that allow the coupler to maintain an acoustical seal and withstand the inward pressure of the ear canal wall while making minimal contact with the ear canal. The invention incorporates a cerumen-protecting feature that prevents damage to a hearing device from infiltration of earwax into the sound port of the receiver. A vent pathway for control of occlusion effects is also provided. A user-friendly, attachment mechanism incorporating a snap-on, twist-off feature allows the acoustic coupler to concentrically surround the receiver module within the ear canal in a space-efficient manner.

28 Claims, 12 Drawing Sheets

MINIMAL CONTACT REPLACEABLE ACOUSTIC COUPLER

TECHNICAL FIELD

The invention relates to earpiece, hearing aid, and audio technology. More particularly, the invention relates to acoustic couplers that seal comfortably and are adapted to be deeply inserted into an individual's ear canal.

BACKGROUND OF THE INVENTION

Two decades ago, most hearing aids dispensed were of the Behind-the-Ear (BTE) type, i.e. a hearing device situated behind the ear with an acoustic tube connecting the device to an earmold placed within the canal. Subsequently, smaller In-the-Ear (ITE) models were introduced. The increasing miniaturization of electronic circuitry and improvements in battery technology have made the development of smaller In-the-Canal (ITC) and Completely-In-the-Canal (CIC) hearing devices possible. The marked reduction in size of these canal devices (both ITC and CIC), coupled with their deep placement within the ear canal, provides an obvious cosmetic advantage to wearers of hearing devices. The reduced residual volume in the ear canal and the proximity of the hearing device receiver (speaker) to the tympanic membrane resulting from deep canal placement of a hearing device provide other advantages, such as improved overall sound fidelity, improved high frequency response, reduced distortion, reduced occlusion effect, improved sound localization, reduced wind noise, and improved use with telephones.

Anatomy of the Ear Canal

FIG. 1 shows a cross section anatomical view of the ear canal along the transverse plane of the head (looking down from top). The ear canal 10 can be described as having two segments. The first segment 11, medial to the canal aperture 12, is surrounded by a cartilaginous tissue 13. The second segment 15, near the tympanic membrane 16, is surrounded by dense bony tissue 17. The tissue 14 lining the cartilaginous region 11 is relatively thick and has a well-developed subcutaneous layer, thus allowing some expansion to occur. In contrast, the tissue 18 lining the bony region 15 is relatively thin and therefore, little or no tolerance for expansion exists in this region. Unlike most illustrations, the external ear canal is rarely a perfect cylindrical or conical shape. While most ear canals are uniquely shaped, having various twists and bends, the ear canal is generally "S" shaped, having a first bend 19 occurring approximately at the aperture 12 of the ear canal, and a second bend 20 occurring at the cartilaginous-bony junction.

The ear canal undergoes substantial deformation within the cartilaginous area of the canal as a result of the jaw motion associated with talking, chewing, yawning, and biting. This deformation is generally caused by asymmetric stresses from the actions of the mandibular condyle on neighboring cartilaginous tissue. The obstacles to coupling sound deeply into the ear canal posed by individual ear canal architecture and dynamic ear canal deformations due to jaw motion represent unsolved challenges to users of current hearing aids and other electroacoustic devices.

The Challenges of Acoustic Coupling within the Ear Canal

Canal hearing devices, either in-the-canal (ITC) or completely-in-the-canal (CIC), must provide adequate acoustic sealing within the ear canal to prevent sound leakage from the receiver (speaker) outlet of the device into the microphone inlet. Such leakage causes acoustic feedback, manifested by an annoying whistling sound. Feedback is a common problem experienced by many hearing aid users. Similarly, in earpieces for use with certain audio and communication devices, adequate sealing deep within the ear canal is required to provide fidelity and efficient sound reproduction.

Most hearing devices available today require custom fabrication to ensure an exact fit of the earpiece to the corresponding ear canal. The fabrication process requires an impression of the ear canal, a procedure that is not only uncomfortable but may even be hazardous to the patient. Using the impression as a template, the manufacturer fabricates a custom device or earmold. Even in custom earpieces or canal devices, small gaps between the earpiece and the wall of the ear canal frequently occur. These gaps, a significant source of acoustic feedback, occur because ear impressions do not mimic the geometry of the ear canal identically. Furthermore, gaps also occur during canal deformations associated with jaw movements. Providing a tighter fit to minimize gaps and improve sealing is usually accompanied by discomfort, irritation, or even pain, particularly in the bony portion of the canal, which is sensitive and more prone to discomfort and irritation.

Feedback is a particular problem for users of canal devices because the microphone sound inlet in canal devices is much closer to the receiver outlet than in a larger device such as a behind-the-ear (BTE) type. The proximity of microphone to receiver in canal devices provides less distance through which acoustic energy must travel from receiver outlet to microphone inlet, increasing the possibility of feedback. Thus, canal devices typically are not recommended for persons with significant hearing losses, since they require greater amplification and thus are more prone to feedback.

Replaceable acoustic couplers that seal and conform to a variety of ear canals are desirable because they eliminate the need for impressions and custom fabrication. Sadly, current attachment mechanisms, including threading or compression fitting of miniature connections, render their application to canal devices impractical due to space limitations within the ear canal or dexterity problems among hearing aid users; particularly the elderly, who represent the largest segment of the hearing impaired population.

DESCRIPTION OF THE PRIOR ART

Several methods have been disclosed for coupling the acoustic output of a receiver into the ear canal. G. Ward and D. McCallister, *Apparatus and Method for Conveying Sound to the Ear*, U.S. Pat. No. 5,031,219 (Jul. 9, 1991) and *Apparatus and Method for Conveying Sound to the Ear*, U.S. Pat. No. 5,201,007 (Apr. 6, 1993) disclose an earmold consisting of an acoustic conduction tube having a flexible flanged tip. The flanged tip conforms to the ear canal to provide an acoustic seal. The earmold of the device as shown in FIGS. 1–6 is designed for coupling serially with a receiver (speaker) presumably positioned outside the ear canal.

Similarly, C. Ahlberg, D. Chamberlin, J. Bushong, R. Oliveira, V. Kolpe; *Hearing Aid Ear Piece Having Disposable, Compressible Polymeric Foam Sleeve*; U.S. Pat. No. 4,880,076 (Nov. 14, 1989); and R. Oliveira, D. Chamberlin, M. Babcock, *Ear Piece Having Disposable, Compressible Polymeric Foam Sleeve*, U.S. Pat. No. 5,002, 151 (Mar. 26, 1991) disclose a replaceable compressible polymeric foam sleeve (FIGS. 1 and 2 in both patents) having a duct 16 formed with a female screw thread 20 which mates with a male screw thread 12 of an earpiece. The receiver, not shown in any of the figures, is presumably either within the ear canal or external thereto, but coupled serially to the replaceable acoustic coupler.

H. Hardt, *Hearing Aid*, U.S. Pat. No. 4,607,720 (Aug. 26, 1986) discloses a silicone rubber sealing plug that is detachably connected to the housing of a hearing aid via a miniature coupling element. The sealing plug is coupled via a snap, friction, or threading mechanism.

There are several significant disadvantages associated with these prior art devices. First among these is the serial positioning of an acoustic coupler with respect to a canal hearing device or earpiece, which not only affects the quality of the sound emitted from the receiver adversely, but also consumes substantial space within the ear canal. Another disadvantage of the prior art is the disclosed attachment methods, which require considerable dexterity for the threading or alignment of miniature connecting parts. This is especially problematic for persons having limited manual dexterity; the elderly or the handicapped for example.

H. Garcia, J. Beumers, R. Claes, *In-the-Ear Hearing Aid with Flexible Seal*, U.S. Pat. No. 5,742,692 (Apr. 21, 1998) disclose an in-the-ear hearing aid having a flexible collar to be positioned deep within the bony portion of the ear canal. In Garcia et al., the wall thickness of the tubular portion and the curved portion of the prior art collar is less than 0.5 mm, and the collar lacks structural components that allow it to resist hoop stresses and maintain its shape within the ear canal. Thus, the collar is rendered ineffectual for assuring improved user comfort or anchoring the hearing device within the ear canal. The thinness of the membrane and the small dimensions of the device render it suitable only for extremely deep placement within the ear canal immediately adjacent the tympanic membrane. The invention is also unsuitable for use by those having limited manual dexterity, requiring the use of a special tool for attachment and removal (col. 5, lines 56–57). The cerumen-protecting feature of the invention is embodied as a labyrinthine pathway from the sound aperture of the sealing collar to the sound aperture of the receiver housing. Such a feature would fail to protect the receiver from cerumen infiltration in the case of a wearer with semi-liquid earwax. A labyrinthine sound pathway would effect sound transmitted to the tympanic membrane from the receiver adversely. The fixing portion of the sealing collar is separately fabricated, presumably from a rigid or a semi-rigid polymer. Contact of such a rigid part with the bony portion of the ear canal or the tympanic membrane may cause discomfort and possibly even trauma to the wearer. Garcia make no provision to vent the ear canal.

J. Sauer, C. Haertl, *Auditory Canal Insert for Hearing Aids*; U.S. Pat. No. 5,654,530 (Aug. 5, 1997) disclose an acoustic sealing ring having "fan-like circumferential segments" fitted within a groove on a hearing device. The invention does not deal with practical methods for easy manipulation of the acoustic seal during its replacement by the hearing impaired with limited dexterity. Furthermore, the known adverse affects of receiver contamination by earwax through the acoustic seal are not addressed in the invention.

A. Shennib, H. Fletcher, Acoustic Coupler; U.S. patent application Ser. No. 08/902,410 (filed Jul. 29, 1997) disclose an acoustic coupler having an improved placement method. The acoustic coupler is radially concentric about a receiver module. The acoustic coupler comprises an acoustic coupler and a coupling sleeve, the coupler sleeve being relatively elastic and thin walled, such that it deforms into an elliptic shape during attachment to the receiver assembly. The acoustic coupler further comprises a debris guard 57 (FIG. 3) for protection of the receiver and collection of environmental and physiologic debris including cerumen (earwax).

S. Rouw, A. Shennib, J. Brown, *Intracanal Acoustic Coupler with Molded Debris Guard*, U.S. patent application Ser. No. 60/088862 (filed Jun. 11, 1998) disclose an acoustic coupler having a debris guard element integral to the acoustic coupler that is also placed concentrically about a receiver module. The acoustic coupler comprises an acoustic coupler made of a compressible material, such as polyurethane foam or silicone, to conform to the shape of ear canal, thus sealing the ear canal.

E. Weeks, *Air Conduction Hearing Device*, U.S. Pat. No. 5,748,743 (May 5, 1998) discloses an acoustic coupler comprising a soft flexible tip which snaps on the earpiece of a hearing aid. The flexible tip of the Weeks invention uniquely combines acoustic sealing with a thin molded wax guard membrane. While the thin membrane (0.01" to 0.001" in thickness) does provide protection from earwax it also attenuates sounds significantly due to its non-porous design. The sound attenuation in Weeks's invention, in the range of 15 dB, represents a greater than 80% loss of acoustic energy. Such inefficiency renders the application of Weeks's flexible tip unacceptable for application in energy efficient hearing aids.

It would be advantageous to provide an improved disposable acoustic coupler for use with an earpiece that incorporates an intracanal receiver module.

SUMMARY OF THE INVENTION

The invention provides an improved disposable acoustic coupler for use with an earpiece that incorporates an intracanal receiver module. The acoustic coupler is adapted to be inserted deeply into the ear canal while making minimal contact with the wall of the ear canal, thus maximizing the user's comfort. Additionally, the acoustic coupler functions to anchor the earpiece in the user's ear canal at a depth of insertion guaranteed to produce optimal acoustic performance. The invention also seals the ear canal acoustically, thereby preventing acoustic feedback. The invention prevents the infiltration of cerumen into the sound port of the receiver, thus eliminating the need for costly and inconvenient repairs to the hearing device. The invention also provides a mechanism for minimizing the so-called occlusion effect.

The acoustic coupler comprises a snap ring in the form of a flattened cylinder and a dome-shaped cap portion. The snap ring and the cap portion are molded as a single integral piece from an elastomer such as silicone rubber. The snap ring is firm enough to maintain its structural integrity during attachment or detachment from the earpiece, while retaining a degree of flexibility and compressibility; and the cap portion is soft and highly compliant, allowing the acoustic coupler to seal the ear canal acoustically. The dome-shaped cap portion incorporates structural ribs to render the cap resistant to hoop stress generated by the pressure of the ear canal wall, while allowing it to be manufactured from a soft, pliable material. The cap also provides a venting system to allow dissipation of the accumulated low-frequency acoustical energy responsible for occlusion effects, and to allow for equalization of intracanal air pressure with that of the external environment.

Attachment of the acoustic coupler to the receiver assembly is performed by applying a minimal axial (push) force to secure the acoustic coupler to the receiver assembly. The coupler remains securely attached and can withstand considerable axial detachment (pull) forces without being dislodged within or outside the ear canal. However, by applying a rotational (twist) force with respect to the receiver housing, the acoustic coupler can be easily detached from the receiver housing. Because rotational movements are minimal during insertion or removal of the coupler from the ear, accidental detachment is not possible. This unique snap-on, twist-off mechanism eliminates the necessity of precisely aligning the acoustic coupler onto the receiver housing, a major benefit to the elderly, who may be visually impaired and/or of limited manual dexterity.

An alternate embodiment of the invention provides a flat cap portion incorporating a beaded edge to maintain structural integrity, such that contact of the acoustic coupler with the ear canal wall is further minimized. A further embodiment provides a cap portion having a concentric ripple that enhances the seal's capacity to accommodate changes in the shape of the ear canal. A still further embodiment of the invention employs a cap portion having a rolled edge.

DETAILED DESCRIPTION

Figure 1:
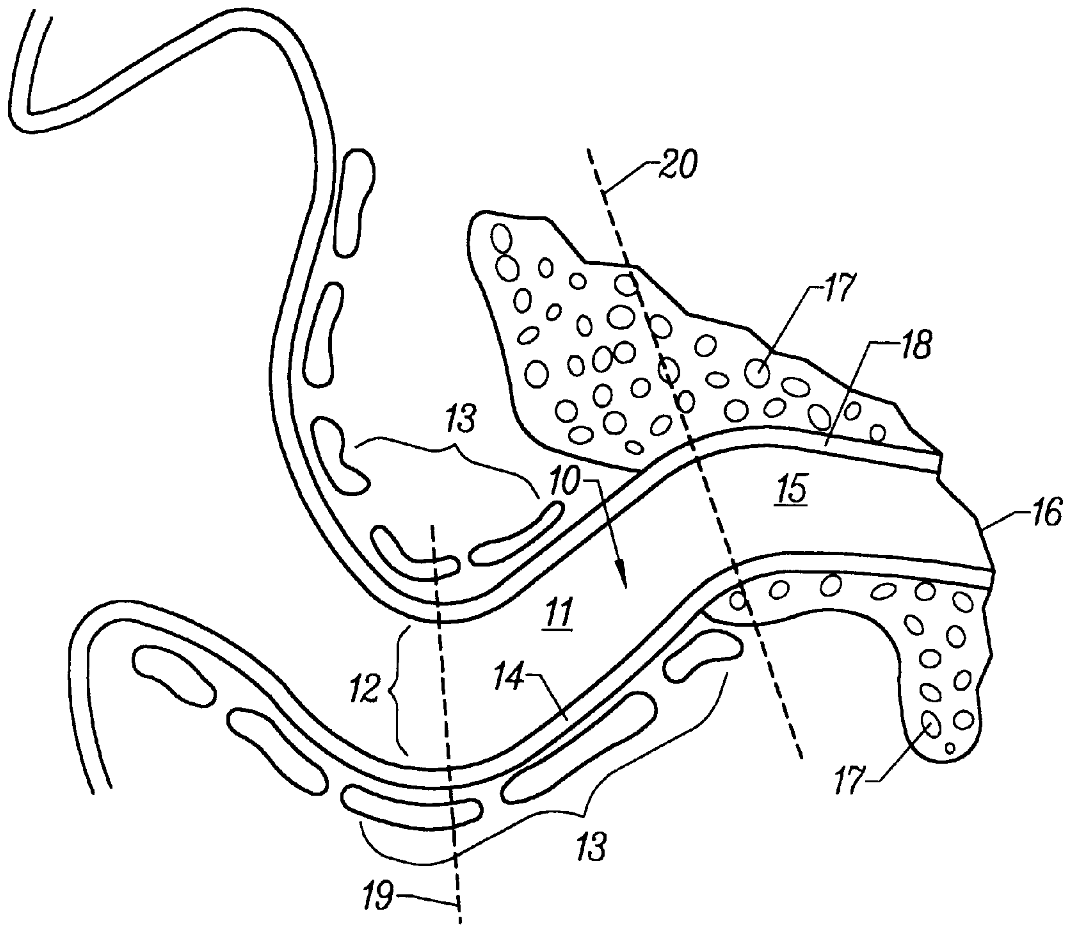
FIG. 1 is a transverse cross section view of an ear canal.
Figure 2:
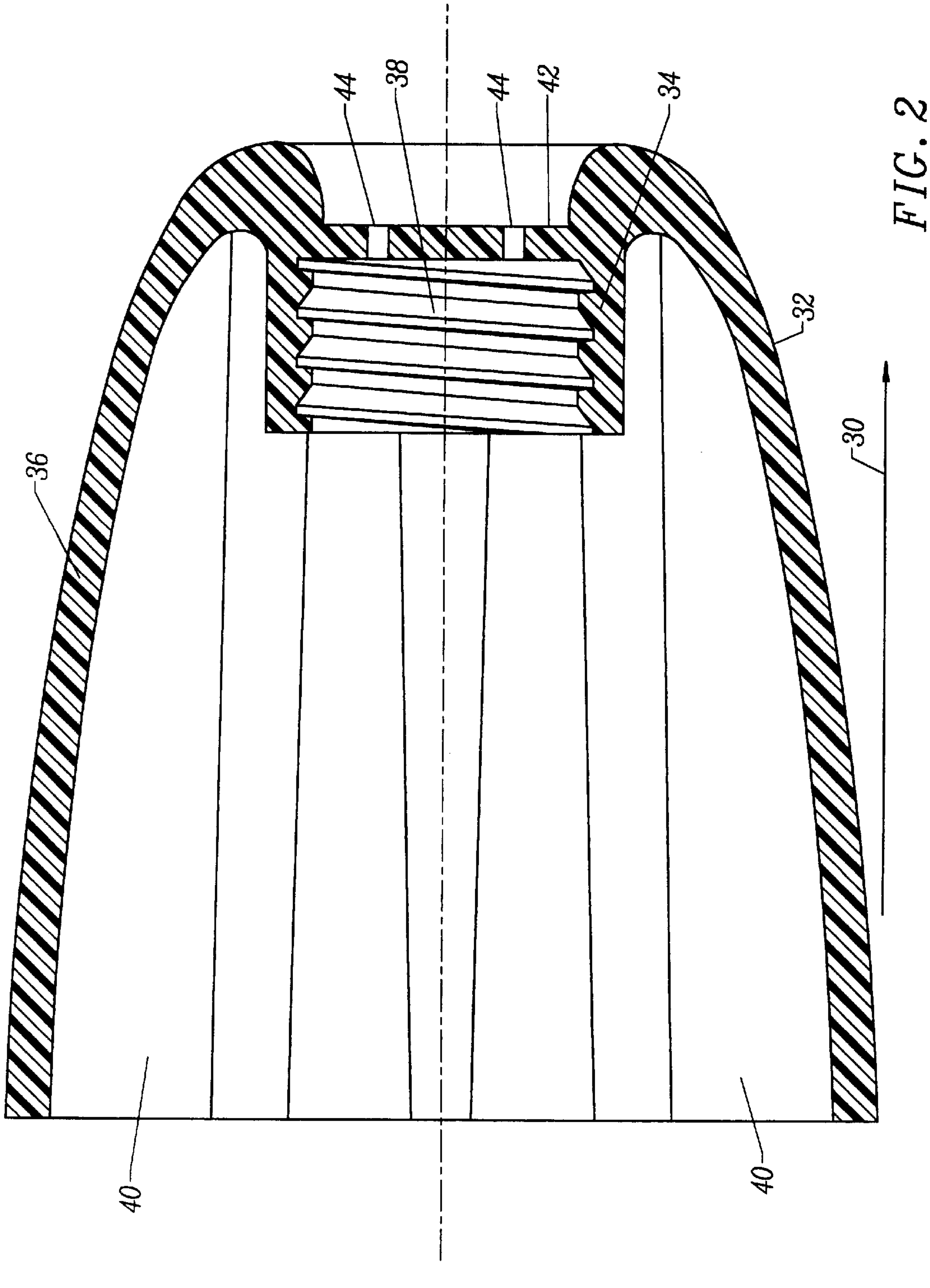
FIG. 2 is a section view of an acoustic coupler according to the invention.

FIG. 2 shows a section view of the preferred embodiment of the invention. Arrow 30 indicates the direction of insertion into the user's ear canal. A threaded snap ring 34 in the form of a flattened cylinder is concentrically surrounded by a dome-shaped cap portion 36 to form the acoustic coupler 32.

The inner surface of the cap portion 36 is configured with a series of structural ribs 40 that are vertically disposed from the medial end to the lateral end of the acoustic coupler 32. The inner surface of the snap ring 34 is configured with female threads 38 that are adapted to mate with a corresponding set of male threads on an intracanal receiver module 46 (see FIG. 5). The invention also provides an integrally-molded debris guard 42 to prevent infiltration of cerumen and other debris into the sound port (not shown) of the receiver module 46. A series of sound aperures 44 allow sound to pass through the debris guard 42 to the ear canal.

Figure 3:
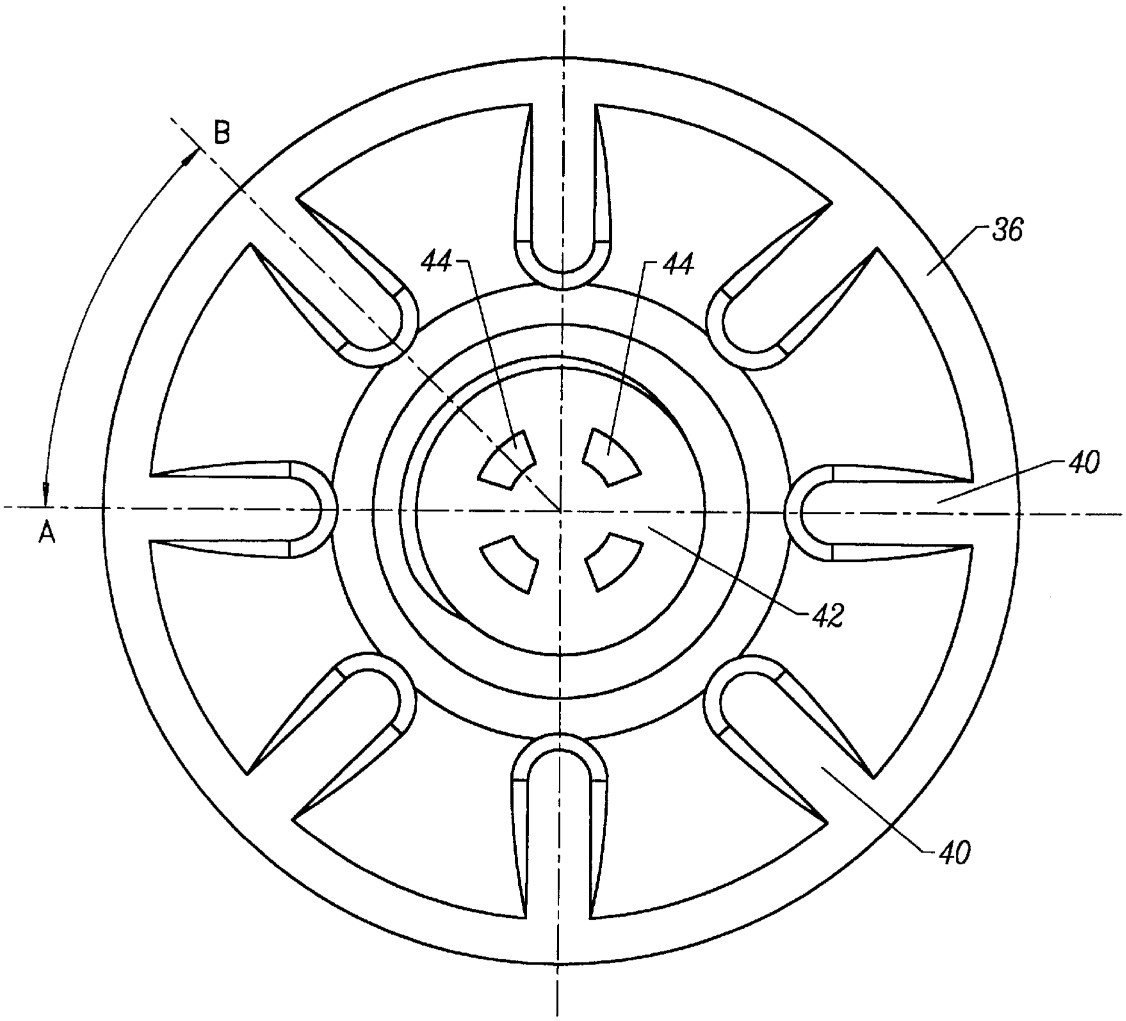
FIG. 3 is an elevation of the acoustic coupler of FIG. 2 from the lateral end according to the invention.

FIG. 3 is an elevation from the lateral end of the invention that shows the structural ribs 40 in cross-section. Each of the ribs 40 is integral with the cap portion 36. Although a cap portion having eight ribs is shown, the actual number of ribs varies according to the size of the acoustic coupler.

Figure 4:
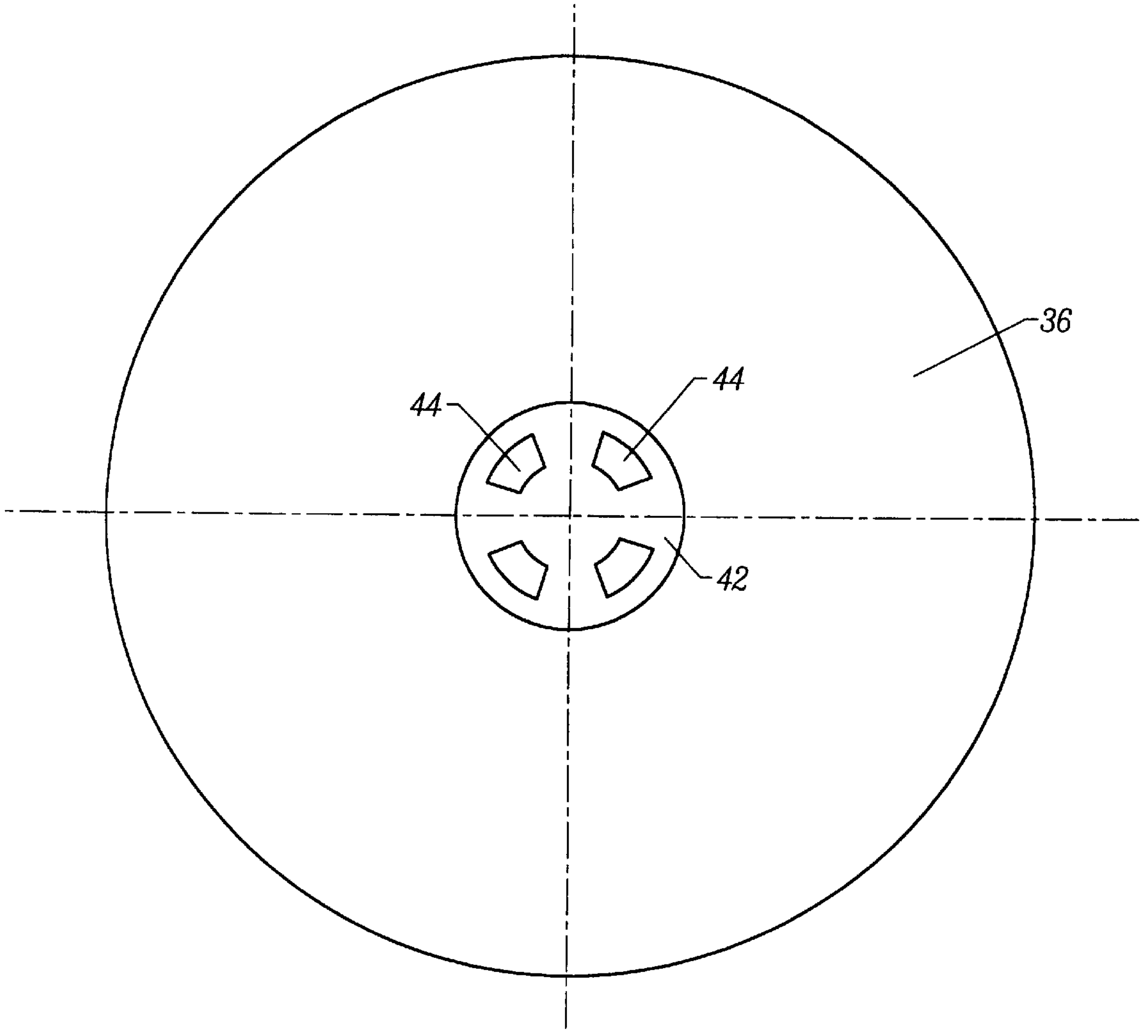
FIG. 4 is an elevation of the acoustic coupler of FIG. 2 from the medial end according to the invention.

FIG. 4 is an elevation from the medial end of the invention that shows the smooth, outer surface of the cap portion 36. Also shown are the series of sound apertures 44 disposed in a circular fashion about the circumference of the debris guard 42 which allows the sound emmitted from the receiver module 46 to pass through the debris guard 44 to the ear canal.

In the preferred embodiment of the invention, the snap ring 34 has a durometer rating of approximately 90 Shore A, allowing it to retain structural integrity during attachment to and detachment from the earpiece, while still retaining a degree of flexibility and compressibility. Although the snap ring 34 and the cap portion 36 are integral to each other, the cap portion must be relatively more pliable than the snap ring in order to conform readily to the varied contours of the user's ear canal, while resting lightly against the canal walls. The cap portion 36 has a durometer rating of approximately 50 Shore A, thus it is soft and highly compliant, allowing the acoustic coupler 32 to be comfortably inserted deep into the ear canal of a hearing aid user. The thickness of the cap portion is also significant in determining the pliability of the cap portion. In the current embodiment of the invention, the cap has a thickness of approximately 0.51 mm. While a soft, compliant cap renders the acoustic coupler easy to insert and remove, and ensures a high degree of user comfort, the coupler must also prevent acoustic feedback by maintaining its structural integrity, all without exerting undue pressure on the walls of the ear canal.

Because the acoustic coupler resides in the ear canal during use, it is subjected to significant hoop stress, i.e. the inward pressure on the seal from the walls of the ear canal. Should the acoustic coupler collapse while in the ear canal, it would no longer isolate the microphone inlet from the output of the intracanal receiver. This would permit leakage of high-frequency acoustical energy. In such event, the hearing aid user would be subjected to the unpleasant, high-pitched whistling associated with acoustic feedback. The cap portion 36 is provided with the structural ribs 40 to ensure that the cap maintains its structural integrity in spite of the inward pressure of the ear canal walls, even though the cap is manufactured from a soft, compliant elastomer. In addition to the structural support provided by the structural ribs 40, the external surface tension of the cap portion 36 lends the acoustical seal additional structural stability.

The manufacturing process employed to achieve the required combination of structural stability and pliability has several unique aspects. The difference between the hardness of the two integrally-molded components is achieved through a process employing well-known insert molding techniques, whereby the snap ring 34 is first molded from a polymer having the requisite hardness characteristic. Then, in a subsequent step, the cap portion 36 is molded onto the snap ring from the same polymer, formulated to the hardness characteristic specific to the cap portion. It is evident from the figures that the outer surface of the cap portion 36 is smooth, while the structural ribs 40 are continuous with the inner surface of the cap portion, forming a series of fin-like projections directed inward toward the receiver module 46 when the earpiece is fully assembled.

The cap portion is molded onto the snap ring with the structural ribs facing outward and the smooth surface facing inward to augment the tension of the external surface of the cap portion. During cooling and curing, the components fuse to form a single unit. After the molded assembly has cooled and cured, the cap portion is folded downward, such that it completely covers and surrounds the snap ring in a skirt-like fashion, with the ribs directed inward and the smooth surface directed to the exterior. The preferred manufacturing material for the invention is silicone rubber, although other thermoplastic elastomers or rubbers, such as SANTOPRENE manufactured by Monsanto Corporation, or LOMOD, manufactured by General Electric Corporation, would also be well-suited.

Figure 5:
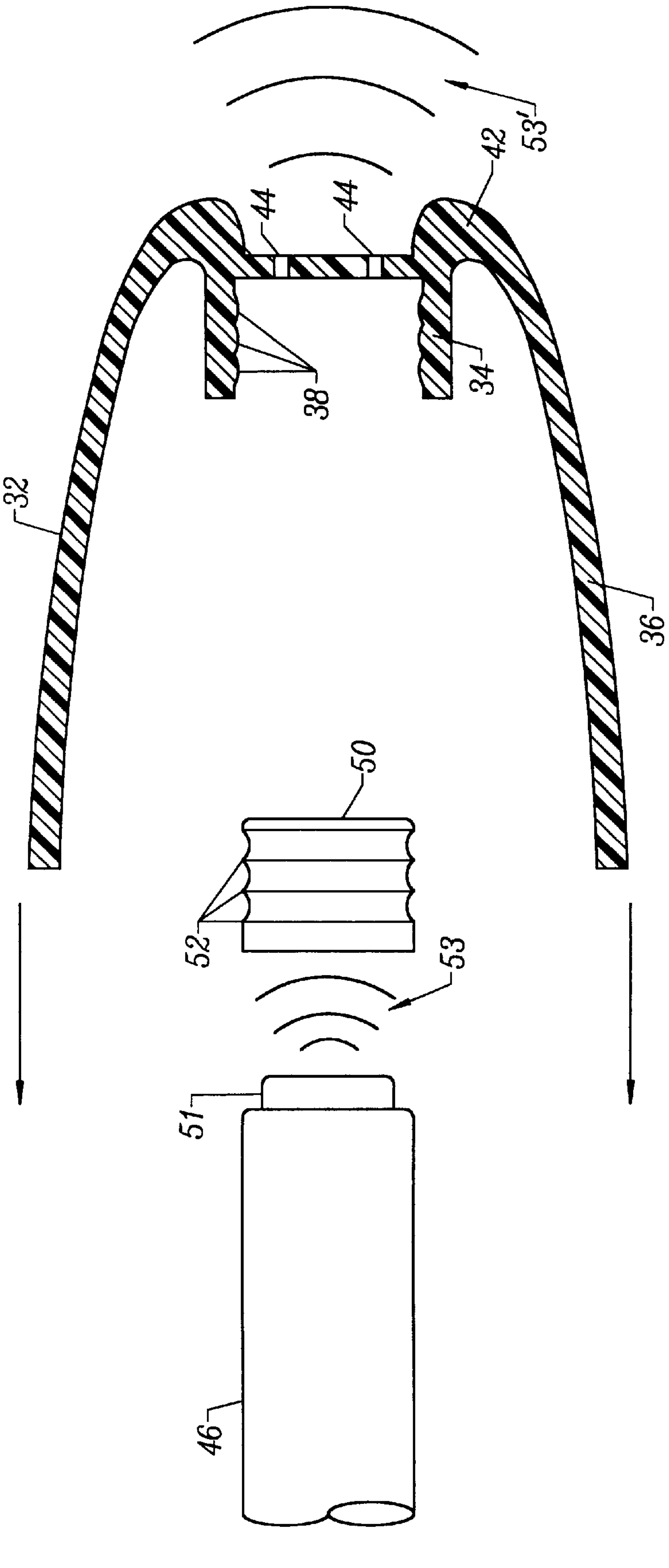
FIG. 5 is an exploded view showing the cooperation of the acoustic coupler of FIG. 2 and an intracanal receiver module according to the invention.

FIG. 5 shows an exploded cross-section of an earpiece comprising the invented acoustic coupler 32 and an intracanal receiver module 46. An adapter sleeve 50 is provided with a set of tapered, male threads 52 adapted to mate with a corresponding set of female threads 38 on the inner surface of the snap ring 34. The adapter sleeve 50 is fixedly attached to the receiver module 46 such that it concentrically surrounds the sound port 51 of the receiver module 46. During the attachment process acoustic coupler 32 is positioned concentrically about the receiver module 46 by mating the tapered male threads 52 with the corresponding female threads 38. During actual use within the ear canal, sound 53 is emitted from the sound port 51 of the receiver module 46. After passing through the sound apertures 44, the sound 53' is delivered into the ear canal of the hearing device user. The integrally-molded debris guard 42 prevents the infiltration of cerumen, sloughed epithelial cells, and other physiologic and environmental debris backward into the sound port of the receiver module 46, while remaining acoustically transparent.

In the current embodiment of the invention, the adapter sleeve 50 is manufactured from electro-less nickel using conventional machining techniques. Other embodiments are possible employing various thermoplastic polymers shaped using conventional, widely-known molding techniques. The adapter sleeve 50 is attached to the receiver module 46 using a spot welding technique, although it could also be attached using a suitable adhesive. The receiver module 46 employs a conventional hearing aid receiver such as the FS series, manufactured by Knowles, Inc. of Itasca Ill.

The earpiece of the invention employs an attachment mechanism similar to that disclosed by Shennib, et al. in U.S. patent application No. 08/902,401 (filed Jul. 29, 1997), assigned to the same assignee as the invention. During the attachment process, the receiver assembly 46 is inserted into the snap ring of the acoustic coupler, as shown in FIGS. 5–8. Attachment is accomplished by applying axial (push) force on the acoustic coupler, causing deformation of the snap ring as it is being pushed against the tapered male thread partially surrounding the receiver assembly.

Figure 6A:
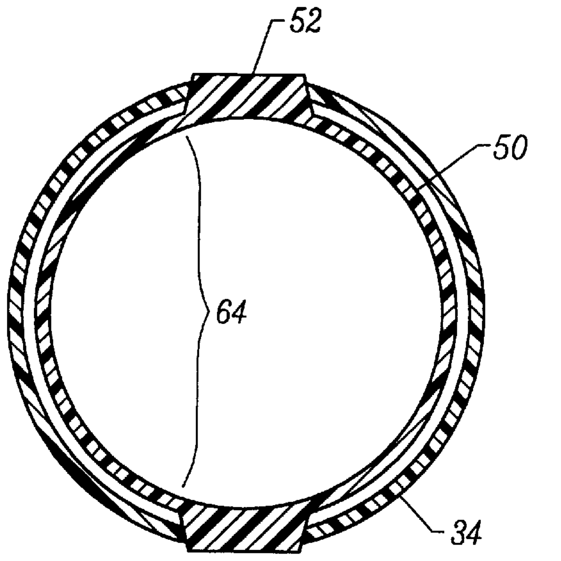
FIGS. 6*a*–6*b* show the cooperation of a threaded snap ring with a threaded adapter sleeve according to the invention.
Figure 6B:
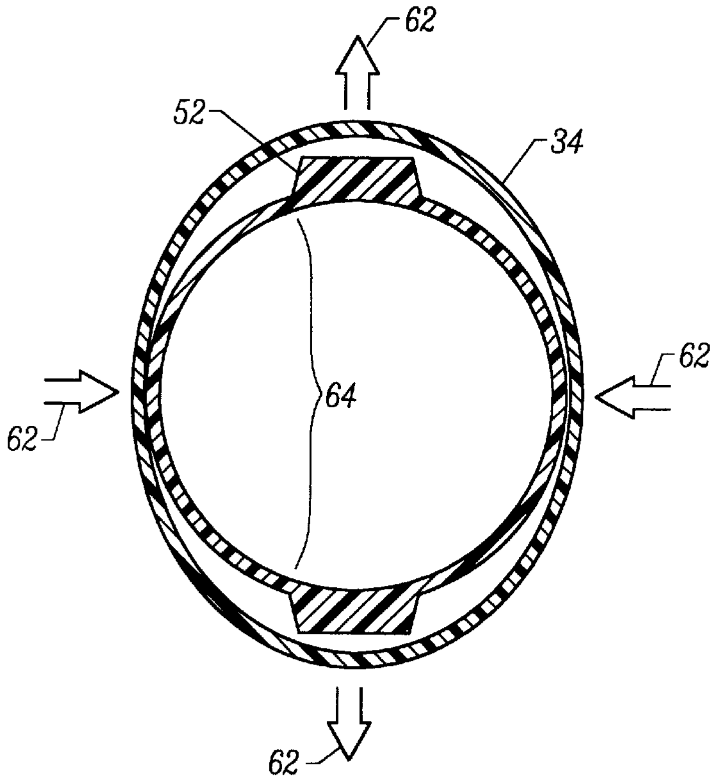
Figure 7:
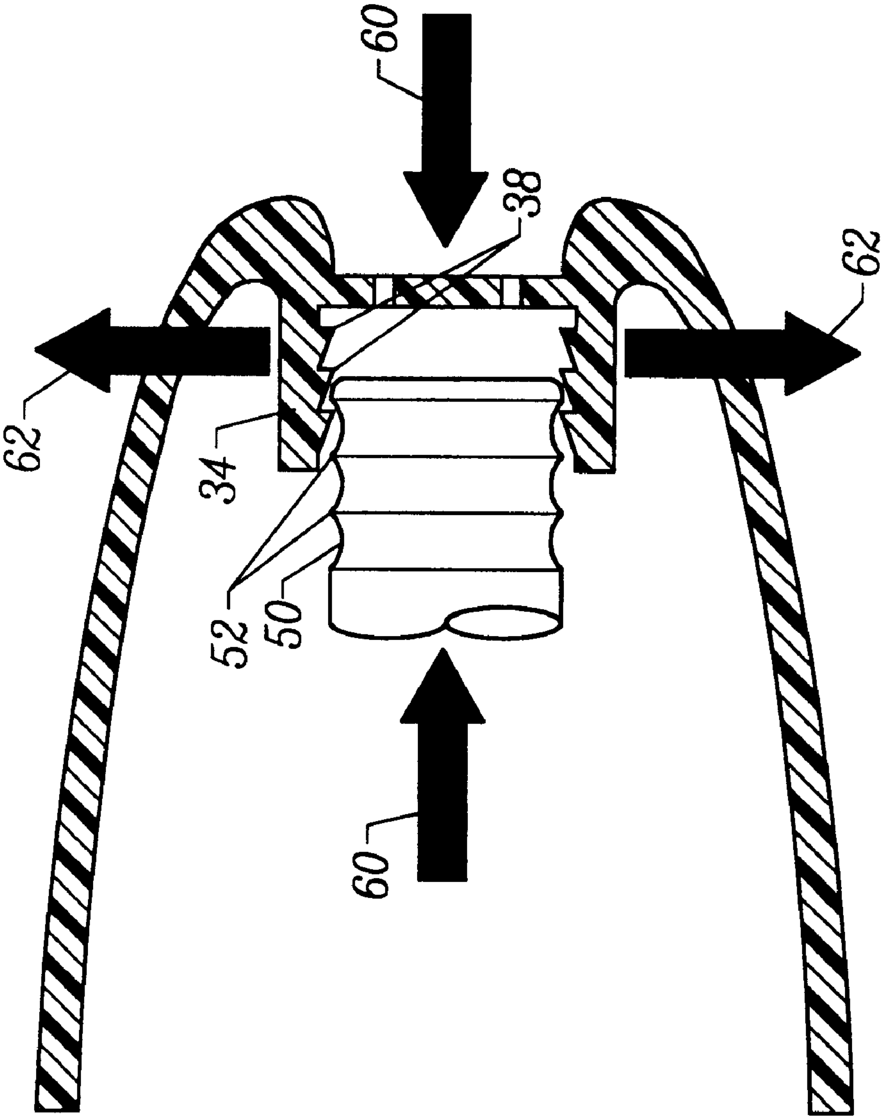
FIG. 7 shows the deformation of the snap ring of FIGS. 6*a*–6*b* in response to axial pressure according to the invention.

As FIGS. 6*a*, 6*b* and 7 illustrate, the axial forces 60 engaging the male threads of the receiver housing create radial forces 62 which deform the elastic snap ring into an elliptical shape (FIG. 6*b*), allowing the snap ring threads to slide over the tapered male threads 52 of the adapter sleeve 50. FIGS. 6*a* and 6*b* show the perimeter of the snap ring 34 during and after the attachment process. The snap ring 34 deforms to an essentially elliptical shape (FIG. 6*b*) as defined by the perimeter of the adapter sleeve 50 with its partial male threads 52 and relieved area 64.

When the acoustic coupler 32 is fully engaged, the snap ring 34 is fully restored to its original cylindrical form (FIG. 6*a*). The mated receiver and snap ring threads, 52 and 38, respectively, ensure secure attachment of the acoustic coupler 32 to the receiver assembly 46. The interlocking, tapered design of the mated threads prevents reasonable pull axial forces from detaching the acoustic coupler, allowing mainly rotational (twist) forces to remove the acoustic coupler.

The invention also provides a mechanism for control of the so-called occlusion effect. The occlusion effect, a phenomenon well known in the hearing aid art, occurs when an individual's ear canal is obstructed by a hearing aid. The hearing aid user perceives that their own voice sounds hollow. As the hearing aid user speaks, self-generated sounds are conducted through the bones of the face and head. The resultant accumulation of low-frequency acoustical energy within the residual space of the ear canal is responsible for the occlusion effect, a significant source of distress and frustration to hearing aid users and dispensing professionals alike. Deep canal placement of a hearing aid may alleviate the occlusion effect somewhat by reducing the size of the residual space in the ear canal, that portion of the ear canal remaining between the hearing aid and the tympanic membrane. It is frequently necessary to provide a vent across the hearing aid in order to allow the accumulated low-frequency acoustical energy within the residual space to dissipate to the external environment.

Figure 8:
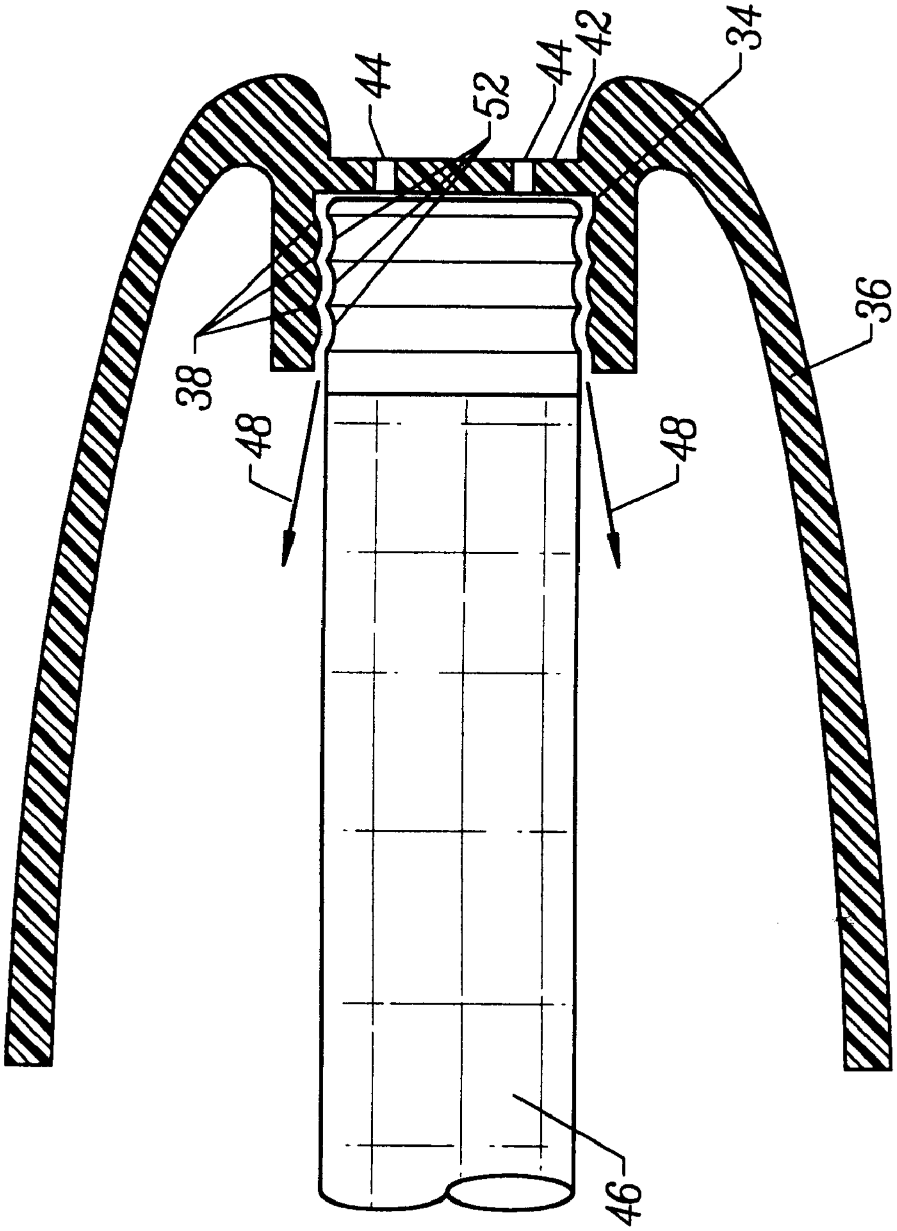
FIG. 8 shows the cooperation of the elements of the invention, fully assembled, according to the invention.

FIG. 8 is a cross-section of a fully assembled earpiece according to the invention. The sound apertures 44 provide a pathway for the rearward diffusion of this accumulated acoustical energy, as indicated by the arrows 48. As shown in FIG. 6*a*, the relieved portion 64 provides an air gap between the snap ring 34 and the adapter sleeve 50. This air gap, combined with the sound apertures 44 provides a route of escape to the external environment for the low frequency acoustical energy responsible for the occlusion effect. It is also important to vent the ear canal to allow the dissipation of accumulated moisture within the ear canal, a possible source of damage to the receiver module 46. Venting the ear canal also safeguards the user from pressure-induced injury to the tympanic membrane that may occur during insertion and removal of the hearing device or during abrupt shifts in atmospheric pressure; for example, during takeoff and landing of an aircraft.

The acoustic coupler is provided in a range of assorted sizes, to accommodate the variety of ear canal shapes and sizes encountered in the general population. Referring to FIG. 3, the distance from point A to point B is the length of the arc along the external circumference of the cap portion from the centerline of one of the structural ribs to the centerline of the adjacent rib. It has been empirically determined that the optimal arc length AB between ribs is approximately 3.6 mm for an acoustic coupler having a cap thickness of approximately 0.51 mm. While it is possible to employ other rib-to-rib distances, the structural integrity of the acoustic coupler may be compromised. Thus, the number of structural ribs provided varies according to the size of the acoustic coupler.

Figure 9:
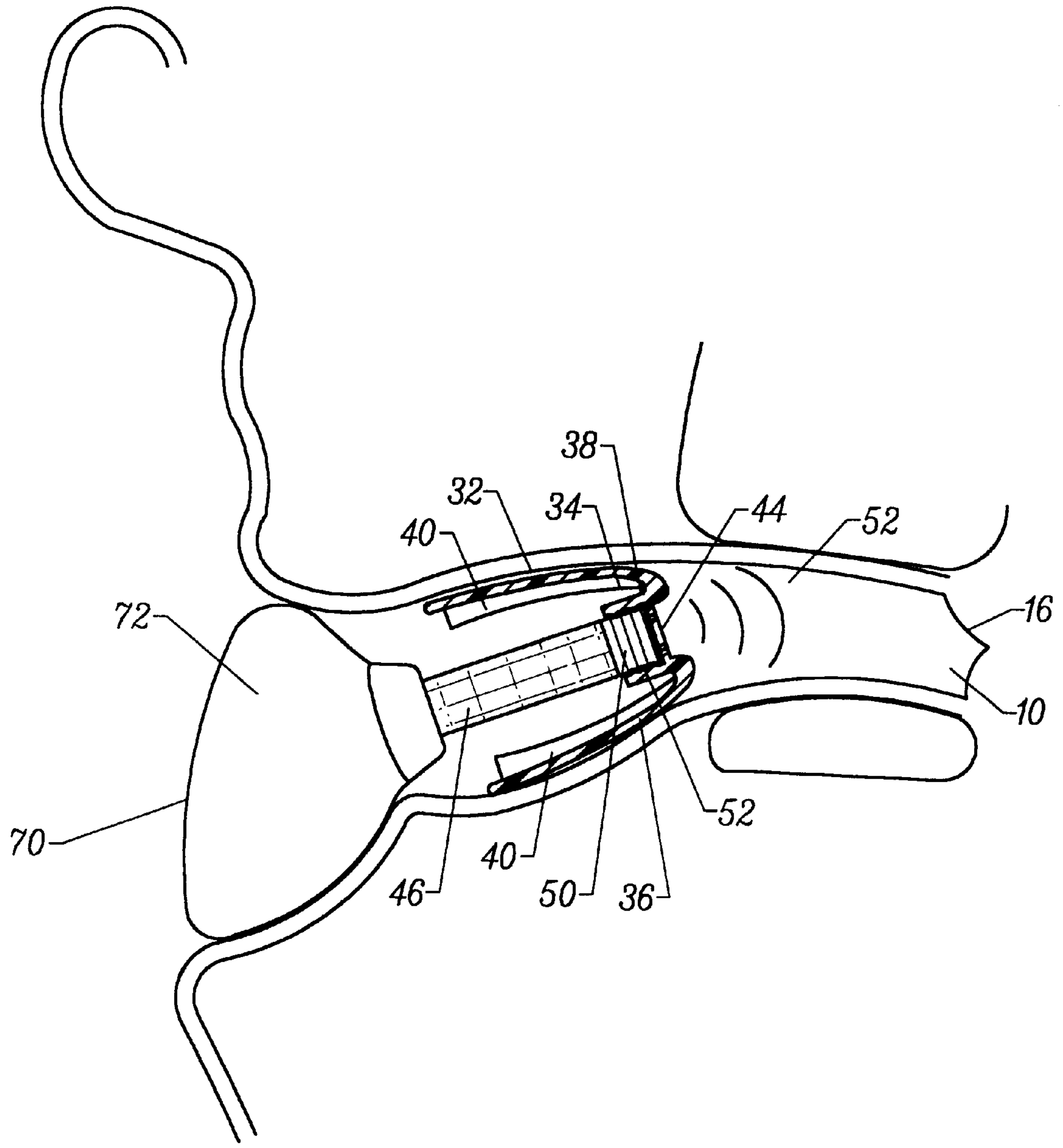
FIG. 9 shows the invention in use within an ear canal according to the invention.

FIG. 9 is a cross-section of an ear canal showing the invention in actual use. A hearing aid 70 comprising an external module 72, an intracanal receiver module, and an acoustic coupler 32 is positioned within the ear canal 10 of a hearing aid user. The external hearing aid module contains the controls, the power supply, and the signal processing circuitry for the hearing aid 70. An adapter sleeve 50 provided with partial, tapered male threads 52 is fixedly attached to the receiver module 46 such that it concentrically surrounds the sound port (not shown) of the intracanal receiver module 46. The corresponding female threads 38 on the inner surface of the snap ring 34 of the acoustic coupler 32 securely attach the acoustic coupler 32 to the intracanal receiver module 46. Sound 53 emitted from the receiver module 46 is delivered in the vicinity of the tympanic membrane 16 after it passes through the sound apertures 44. After insertion, the compliant cap portion 36 conforms to the shape of the ear canal 10, lightly contacting the canal walls and acoustically sealing the ear canal. The structural ribs 40 support the cap portion and prevent it from collapsing or folding, thus maintaining the acoustic coupler and anchoring the hearing aid 70 in the ear canal.

Alternate Embodiments of the Invention

Figure 10:
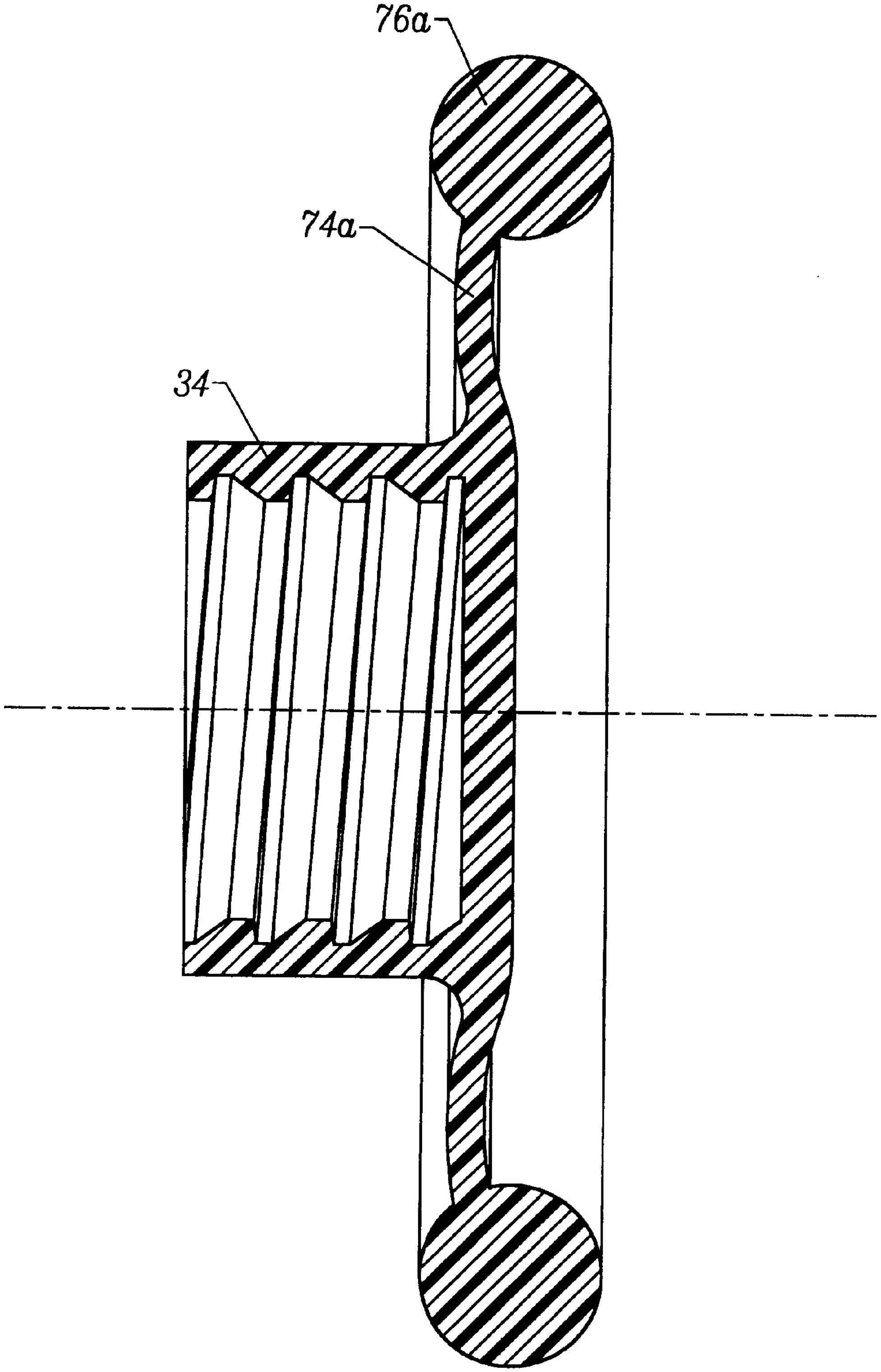
FIGS. 10–12 are alternative embodiments of an acoustic coupler according to the invention.
Figure 11:
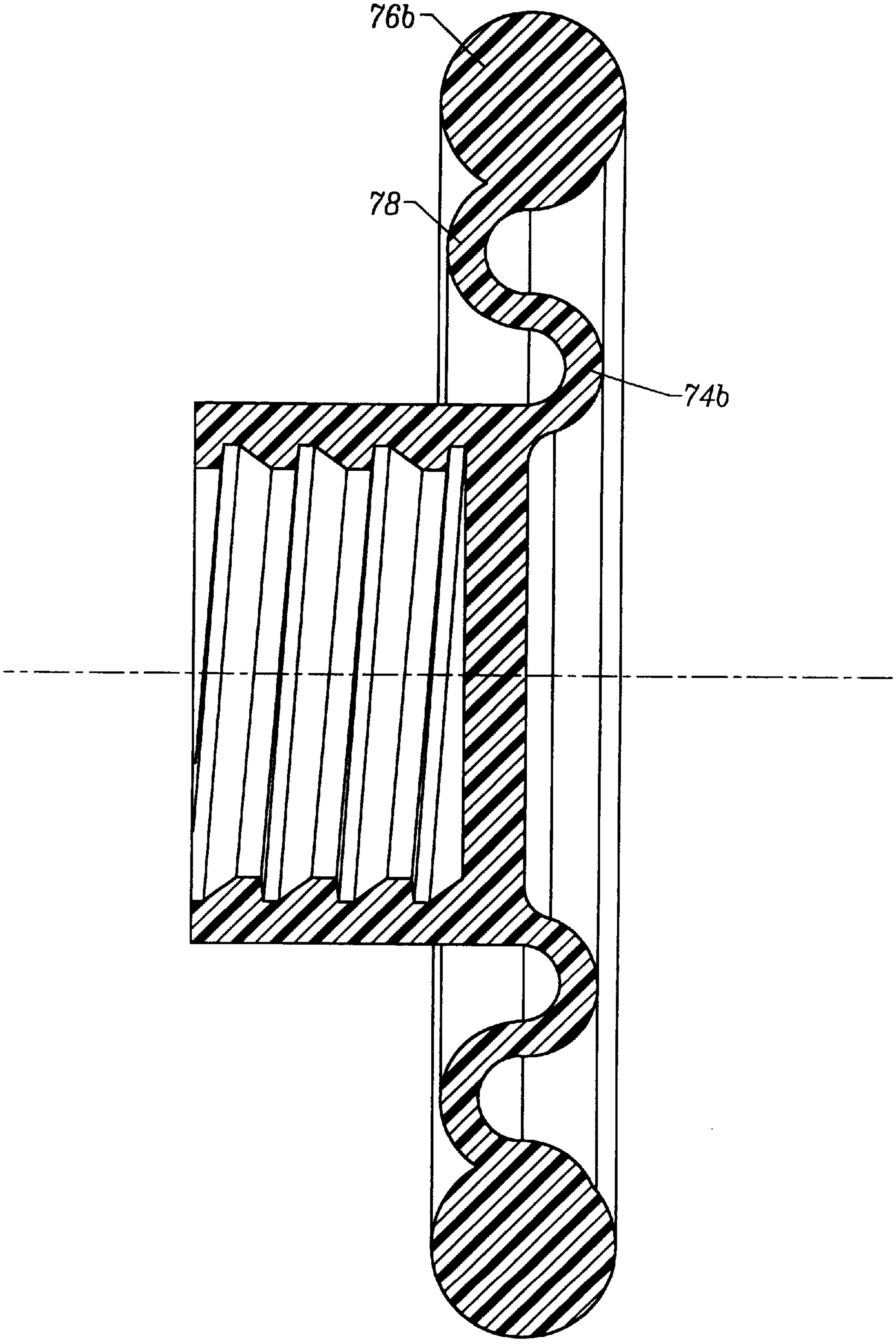
Figure 12:
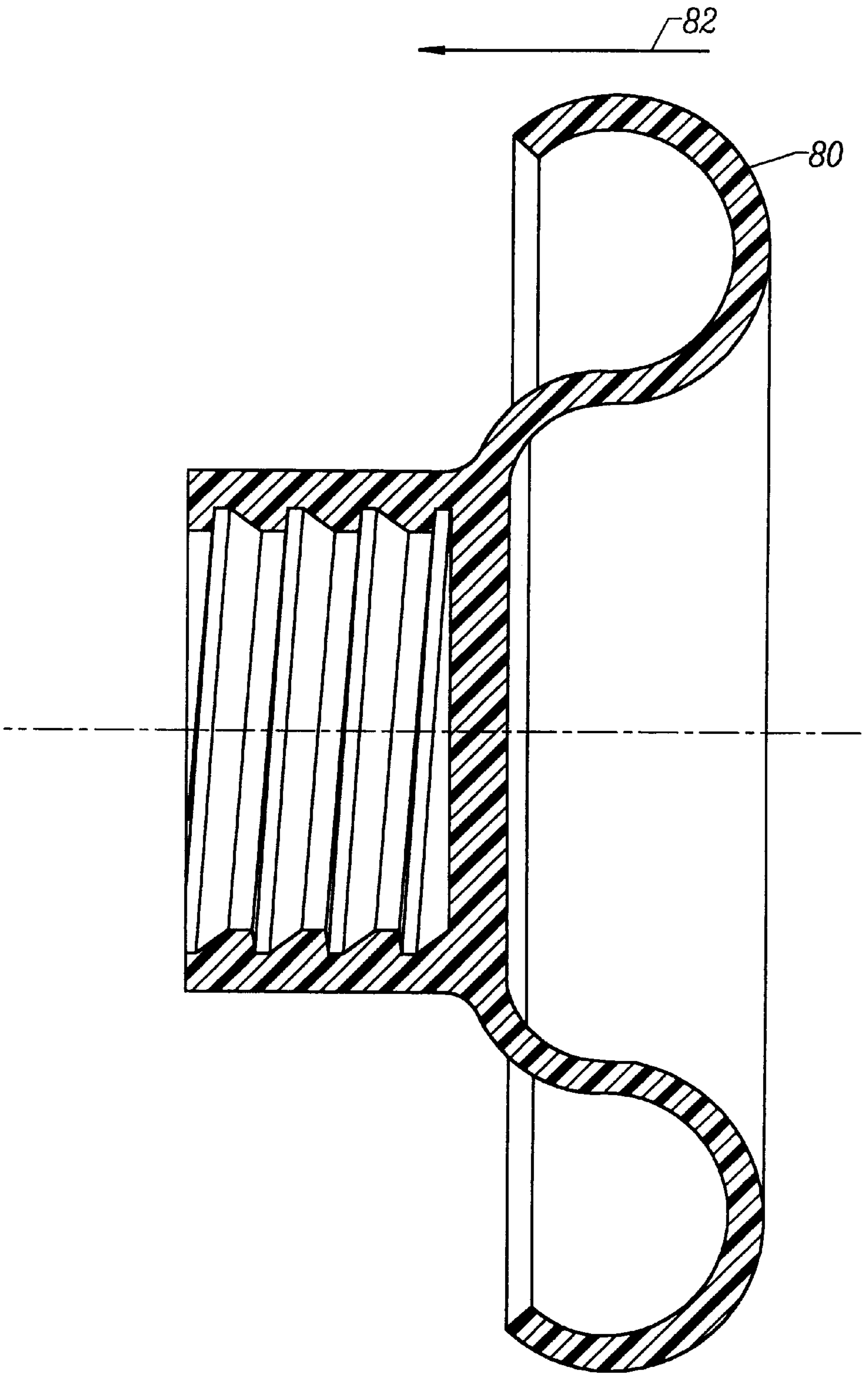

FIGS. 10–12 depict a series of alternate embodiments of the invention. All of the alternate embodiments incorporate a threaded snap ring 34 as in the preferred embodiment.

The embodiment shown in FIG. 10 provides a circular diaphragm 74*a* continuously molded with the snap ring 34. A bead 76*a* around the outside edge of the diaphragm 74*a* lends the acoustic coupler additional structural support. In this way, the contact with the ear canal wall is further minimized while still anchoring the hearing device in the ear canal and maintaining an acoustic seal.

FIG. 11 shows an acoustic coupler having a circular diaphragm 74*b* reinforced by a bead 76*b*. The diaphragm 74*b* is provided with a concentric ripple 78 that grants the receiver module additional freedom of movement within the ear canal, both axially (back and forth) and radially (from one wall to the other). In this way the hearing device is able to float within the ear canal in response to changes in the shape of the ear canal secondary to jaw movements.

FIG. 12 shows an acoustic coupler providing a molded cuff 80. As the hearing device is inserted and advanced within the ear canal, the cuff 80 is drawn backward in the direction of the arrow 82 and forms a tight seal within the ear canal.

The invention and its various embodiments offer numerous advantages.

The invention makes it possible to retain a receiver module in the ear canal for extended periods of time without subjecting the user to an intolerable level of discomfort. Thus the user is able to take full advantage of the beneficial effect on sound quality of deep canal placement of a hearing device.

The acoustic coupler anchors the hearing device at an optimal depth of insertion without resort to a custom earmold, greatly simplifying the process of fitting canal hearing devices and sparing the user considerable discomfort, expense and inconvenience.

The use of a replaceable acoustic coupler to seal the ear canal acoustically makes high-quality, mass-produced canal hearing devices entirely practical for the first time.

Fabricating the acoustic coupler from a soft pliable elastomer such as silicone rubber allows the acoustic coupler to conform to the walls of the ear canal without discomfort to the user. The structural ribs of the invention guarantee the integrity of the acoustic seal, sparing the user the unpleasantness of acoustic feedback, without exerting undue pressure on the walls of the ear canal.

Incorporating a cerumen-protecting debris guard into the design of the acoustic coupler minimizes the possibility that the canal device will be damaged from earwax infiltration, sparing the user the considerable inconvenience and expense of having the hearing device repaired.

The ear canal venting mechanism of the invention mitigates the undesirable acoustic effects of occluding the ear canal with a hearing device, historically a source of deep dissatisfaction to users of hearing aids.

The snap-on, twist-off attachment mechanism simplifies the process of removing and replacing the acoustic coupler, making the invention especially well-suited for use by those lacking manual dexterity, such as the elderly or the physically-handicapped.

The various embodiments of the invention further minimize the contact of the acoustic coupler with the walls of the ear canal, resulting in an acoustic coupler that is lightweight, highly-space efficient, and very comfortable to use within the ear canal for extended periods of time.

Although the invention is described herein with reference to certain embodiments thereof, one skilled in the art will readily derive other embodiments and applications without departing from the spirit and scope of the invention. Accordingly, the invention should only be limited to the Claims included below.

What is claimed is:

1. An acoustic coupler for use with an earpiece, comprising:

a snap ring comprising a flattened cylinder; and a cap;

wherein said snap ring and said cap are formed as a single integral piece; and an integrally-molded debris guard for preventing infiltration of cerumen and other debris into a sound port of a receiver module.

2. The acoustic coupler of claim 1, wherein said snap ring and said cap are molded from an elastomer.

3. The acoustic coupler of claim 2, wherein said elastomer is silicone rubber.

4. The acoustic coupler of claim 1, wherein said snap ring is firm enough to maintain its structural integrity during attachment or detachment from said earpiece, while retaining a degree of flexibility and compressibility; and wherein said cap is soft and highly compliant, allowing said acoustic coupler to seal a user's ear canal acoustically.

5. The acoustic coupler of claim 1, wherein said cap further comprises structural ribs that render said cap resistant to hoop stress generated by pressure of a user's ear canal wall, while allowing said cap to be manufactured from a soft, pliable material.

6. The acoustic coupler of claim 1, wherein said cap further comprises a venting system for providing dissipation of accumulated low-frequency acoustical energy responsible for occlusion effects, and for providing equalization of intracanal air pressure with that of an external environment.

7. The acoustic coupler of claim 1, wherein attachment of said acoustic coupler to said earpiece is performed by applying a minimal axial (push) force to secure said acoustic coupler to said earpiece;

wherein said acoustic coupler remains securely attached to said earpiece and can withstand considerable axial detachment (pull) forces without being dislodged within or outside a user's ear canal; and wherein said acoustic coupler is removed from said earpiece by applying a rotational (twist) force with respect to said earpiece.

8. The acoustic coupler of claim 1, wherein said cap is dome-shaped.

9. The acoustic coupler of claim 1, wherein said cap is a flat cap having a beaded edge for maintaining structural integrity;

wherein contact of said acoustic coupler with a user's ear canal wall is minimized.

10. The acoustic coupler of claim 1, wherein said cap further comprises a concentric ripple that enhances said acoustic coupler's capacity to accommodate changes in the shape of a user's ear canal.

11. The acoustic coupler of claim 1, wherein said cap has a rolled edge.

12. The acoustic coupler of claim 1, wherein said earpiece is a hearing aid that incorporates an intracanal receiver module.

13. The acoustic coupler of claim 1, wherein said earpiece is an earphone.

14. The acoustic coupler of claim 1, wherein an inner surface of said cap comprises a series of structural ribs that are vertically disposed from a medial end to a lateral end of said acoustic coupler.

15. The acoustic coupler of claim 1, wherein an inner surface of said snap ring comprises female threads that are adapted to mate with a corresponding set of male threads on an intracanal receiver module.

16. The acoustic coupler of claim 1, wherein a series of sound apertures allow sound to pass through said debris guard to a user's ear canal.

17. The acoustic coupler of claim 16, wherein said sound apertures are disposed in a circular fashion about a circumference of said debris guard to allow sound emmitted from said receiver module to pass through said debris guard to said user's ear canal.

18. The acoustic coupler of claim 1, wherein said snap ring has a durometer rating of approximately 90 Shore A.

19. The acoustic coupler of claim 1, wherein said cap has a durometer rating of approximately 50 Shore A.

20. The acoustic coupler of claim 1, wherein said cap has a thickness of approximately 0.51 mm.

21. The acoustic coupler of claim 1, further comprising:

an adapter sleeve having a set of tapered, male threads that are adapted to mate with a corresponding set of female threads on an inner surface of said snap ring;

wherein said adapter sleeve is fixedly attached to a receiver module such that it concentrically surrounds a sound port of said receiver module.

22. The acoustic coupler of claim 1, further comprising:

a circular diaphragm that is continuously molded with said snap ring, wherein a bead around an outside edge of said diaphragm provides additional structural support to said acoustic coupler.

23. The acoustic coupler of claim 22, wherein said diaphragm further comprises a concentric ripple that grants the receiver module additional freedom of movement within a user's ear canal, both axially (back and forth) and radially (from one wall to the other).

24. The acoustic coupler of claim 1, further comprising:

a molded cuff for forming a tight seal within a user's ear canal.

25. An acoustic coupler for use with an earpiece, comprising:

a snap ring, comprising a flattened cylinder; and a cap, wherein said cap further comprises structural ribs that render said cap resistant to hoop stress generated by pressure of a user's ear canal wall, while allowing said cap to be manufactured from a soft pliable material;

wherein said snap ring and said cap are molded as a single, integral piece;

wherein said snap ring and said cap are molded from an elastomer;

wherein said snap ring is firm enough to maintain its structural integrity during attachment or detachment from said earpiece, while retaining a degree of flexibility and compressibility;

wherein said cap is soft and highly compliant, allowing said acoustic coupler to seal a user's ear canal acoustically; and an integrally-molded debris guard for preventing infiltration of cerumen and other debris into a sound port of a receiver module.

26. A method for acoustically coupling sound to a user's ear canal from an earpiece, comprising the steps of:

providing a snap ring, comprising a flattened cylinder; and providing a cap, wherein said cap further comprises structural ribs that render said cap resistant to hoop stress generated by pressure of a user's ear canal wall, while allowing said cap to be manufactured from a soft pliable material;

wherein said snap ring and said cap are molded as a single, integral piece;

wherein said snap ring and said cap are molded from an elastomer;

wherein said snap ring is firm enough to maintain its structural integrity during attachment or detachment from said earpiece, while retaining a degree of flexibility and compressibility;

wherein said cap is soft and highly compliant, allowing said acoustic coupler to seal a user's ear canal acoustically; and providing an integrally-molded debris guard for preventing infiltration of cerumen and other debris into a sound port of a receiver module.

27. The method of claim 26, further comprising the step of:

applying a minimal axial (push) force to secure said acoustic coupler to said earpiece;

wherein said acoustic coupler remains securely attached to said earpiece and can withstand considerable axial detachment (pull) forces without being dislodged within or outside a user's ear canal; and wherein said acoustic coupler is removed from said earpiece by applying a rotational (twist) force with respect to said earpiece.

28. The method of claim 26, further comprising the step of:

acoustically sealing said ear canal of said user by positioning said earpiece deeply within said ear canal of said user such that said acoustic coupler is substantially in direct contact with a wall of said ear canal, allowing said acoustic coupler to prevent leakage to an external environment of high-frequency sound emitted from said earpiece.

* * * * *